US009483851B2

United States Patent
Gao et al.

(10) Patent No.: US 9,483,851 B2
(45) Date of Patent: Nov. 1, 2016

(54) SYSTEMS AND METHODS FOR FILTERING FOR IMAGE GENERATION

(71) Applicant: General Electric Company, Schenectady, NY (US)

(72) Inventors: Hewei Gao, Waukesha, WI (US); Adam Cohen, Waukesha, WI (US); Brian Edward Nett, Waukesha, WI (US); Paavana Sainath, Oconomowoc, WI (US); Yasuhiro Imai, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 94 days.

(21) Appl. No.: 14/330,198

(22) Filed: Jul. 14, 2014

(65) Prior Publication Data
US 2016/0012615 A1  Jan. 14, 2016

(51) Int. Cl.
*G06T 11/00* (2006.01)
*A61B 6/03* (2006.01)
*A61B 6/00* (2006.01)

(52) U.S. Cl.
CPC .......... *G06T 11/005* (2013.01); *A61B 6/032* (2013.01); *A61B 6/5205* (2013.01); *G06T 2211/416* (2013.01)

(58) Field of Classification Search
CPC .......... G06T 7/0012; G06T 11/008; G06T 2211/408; G06T 11/005; G06T 2211/416; A61B 6/03; A61B 6/032; A61B 6/5205
USPC ....... 382/131, 173, 181, 128, 260, 263, 266, 382/269
See application file for complete search history.

(56) References Cited

U.S. PATENT DOCUMENTS

| | | | |
|---|---|---|---|
| 5,907,593 A | 5/1999 | Hsieh et al. | |
| 6,035,012 A * | 3/2000 | Hsieh | A61B 6/5258 378/4 |
| 6,266,388 B1 * | 7/2001 | Hsieh | A61B 6/032 378/15 |

(Continued)

OTHER PUBLICATIONS

Kim, Jung Kuk, Jeffrey A. Fessler, and Zhengya Zhang. "Forward-projection architecture for fast iterative image reconstruction in X-ray CT." Signal Processing, IEEE Transactions on 60.10 (2012): 5508-5518.*

(Continued)

*Primary Examiner* — Bhavesh Mehta
*Assistant Examiner* — Narek Zohrabyan
(74) *Attorney, Agent, or Firm* — Dean D. Small; The Small Patent Law Group, LLC

(57) ABSTRACT

A method is provided including acquiring imaging data of an object to be imaged from a computed tomography (CT) detector. The method also includes reconstructing the acquired imaging data into an initial reconstruction image, and performing material characterization of an image volume of the initial reconstruction image to provide a re-mapped image volume. Further, the method includes performing forward projection on the re-mapped image volume to provide forward projection data, and providing an error projection based on the forward projection data. Also, the method includes filtering at least one of the initial reconstruction image, the re-mapped image volume, the forward projection data, or the error projection. The method also includes using the error projection to update the initial reconstruction image to provide an updated reconstruction image.

20 Claims, 8 Drawing Sheets

(56) References Cited

U.S. PATENT DOCUMENTS

| | | | |
|---|---|---|---|
| 7,298,812 B2 | 11/2007 | Tkaczyk et al. | |
| 7,315,604 B2 | 1/2008 | Raupach | |
| 7,391,844 B2 | 6/2008 | Wu et al. | |
| 7,444,010 B2 | 10/2008 | De Man | |
| 7,466,793 B2 | 12/2008 | Wu et al. | |
| 7,747,057 B2 | 6/2010 | Wu et al. | |
| 2005/0123215 A1* | 6/2005 | Man | G06T 11/005 382/275 |
| 2005/0238133 A1* | 10/2005 | Koppe | G06T 7/0081 378/4 |
| 2007/0274581 A1* | 11/2007 | Wu | G06T 11/008 382/131 |
| 2008/0273651 A1* | 11/2008 | Boas | G06T 11/005 378/4 |
| 2009/0207969 A1* | 8/2009 | Fischer | A61B 6/502 378/37 |
| 2009/0214095 A1 | 8/2009 | Wu et al. | |
| 2009/0225934 A1* | 9/2009 | Hugg | A61B 6/032 378/20 |
| 2010/0061610 A1* | 3/2010 | Van De Haar | G01N 23/046 382/131 |
| 2011/0052022 A1 | 3/2011 | Xu et al. | |
| 2011/0081071 A1 | 4/2011 | Benson et al. | |
| 2011/0293160 A1* | 12/2011 | Bruder | A61B 6/032 382/131 |
| 2012/0308101 A1* | 12/2012 | Zeng | G06T 11/008 382/131 |
| 2012/0314921 A1* | 12/2012 | Star-Lack | G06T 11/005 382/131 |
| 2013/0243293 A1* | 9/2013 | Dennerlein | G06T 11/008 382/131 |
| 2013/0308845 A1* | 11/2013 | Lenox | A61N 5/1039 382/131 |
| 2014/0133719 A1 | 5/2014 | Wu et al. | |
| 2014/0270440 A1* | 9/2014 | Inglese | A61B 6/4241 382/131 |
| 2015/0078507 A1* | 3/2015 | Kyriakou | A61B 6/4085 378/4 |

OTHER PUBLICATIONS

Kasperl et al, "Computed Tomography Metrology in Industrial Research & Development", International Symposium on NDT in Aerospace, pp. 1-8, Dec. 2008.

Stenner et al, "Dynamic iterative beam hardening correction (DIBH-C) for an optimized assessment of cardiac perfusion in ECG-correlated CT", Nuclear Science Symposium Conference Record (NSS/MIC), IEEE, pp. 3523-3530, 2009.

Dembowski et al, "IAR-Artifact Reductions in Computed Tomography", Frauhofer EXRT, pp. 1-6, Apr. 2010.

"Krumm et al, Beam hardening correction of multi-material objects", 10th European Conference on Non-Destructive Testing ECNDT, pp. 1-7-, 2010.

"CT metal artifact reduction method correcting for beam hardening and missing projections", Authors Joost M. Verburg and Joao Seco, Published Apr. 18, 2012 in Physics in Medicine and Biology.

"Reduction in computed tomography metal artifacts due to the Fletcher-Suit application in gynecology patients receiving intracavitary brachytherapy", Authors John Roeske, Christina Lund, Charles Pelizzari, Xiaochan Pan, Arno Mundt, Aug. 2003.

"Minimizing CLip Artifacts in Multi CT Angiography of Clipped Patients", Authors van der Schaaf, van Leeuwen, Vlassenbroek, Velthuis, Published Jan. 2006 issue of AJNR.

* cited by examiner

SYSTEMS AND METHODS FOR FILTERING FOR IMAGE GENERATION

BACKGROUND OF THE INVENTION

The subject matter disclosed herein relates generally to systems and methods for computed tomography (CT) imaging, and for filtering of data acquired by or associated with CT imaging.

In CT imaging, an X-ray source may be rotated around an object to obtain imaging information. X-rays from the source attenuated by the object may be collected or detected by a detector and used to reconstruct an image. As part of image reconstruction, multi-material correction (MMC) may be performed. MMC helps address, for example, the heel effect (e.g., improving houndsfield unit (HU) uniformity across Z-coverage), as well as other issues affecting accurate image reconstruction.

Ideally, for high quality correction performance, during the implementation of a MMC algorithm, the reconstruction displayed field of view (DFOV) should be relatively large, for example, about 70 centimeters. Accordingly, the reconstruction size (or pixel matrix) may need to be increased to maintain a same or even higher pixel resolution as a final reconstruction image. However, practical difficulties are encountered in increasing pixel matrix size, for example due to practical restrictions or limitations on memory and/or computational time. For example, in certain conventional systems, to accelerate reconstruction speed, a pixel matrix of about 320×320 may be employed. Due to, for example, computational time restrictions, utilization of a large DFOV but a small reconstruction size may be impractical to achieve. Due to the limited spatial resolution in conventional first-pass initial image reconstruction, artifacts may appear in MMC corrected images. For example, jagged artifacts, which may appear in the presence of metal, may appear. As another example, undershoots, which may appear near sharp boundaries (e.g., a bone/brain interface), may also appear.

BRIEF DESCRIPTION OF THE INVENTION

In one embodiment, a method is provided that includes acquiring imaging data of an object to be imaged from a computed tomography (CT) detector. The method also includes reconstructing, with at least one processing unit, the acquired imaging data into an initial reconstruction image, and performing, with the at least one processing unit, material characterization of an image volume of the initial reconstruction image to provide a re-mapped image volume from the initial reconstruction image. Further, the method includes performing, with the at least one processing unit, forward projection on the re-mapped image volume to provide forward projection data, and providing, with the at least one processing unit, an error projection based on the forward projection data. Also, the method includes filtering at least one of the initial reconstruction image, the re-mapped image volume provided by performing the material characterization of the image volume, wherein the filtering the re-mapped image volume is performed before performing the forward projection, the forward projection data provided by performing the forward projection on the re-mapped image volume, wherein the filtering the forward projection data is performed before applying the correction, or the error projection. The method also includes using the error projection to update the initial reconstruction image to provide an updated reconstruction image.

In another embodiment, a tangible and non-transitory computer readable medium includes one or more computer software modules configured to direct one or more processors to acquire imaging data of an object to be imaged from a computed tomography (CT) detector. The one or more computer software modules are also configured to direct the one or more processors to reconstruct the acquired imaging data into an initial reconstruction image and to perform material characterization of an image volume of the initial reconstruction image to provide a re-mapped image volume from the initial reconstruction image. The one or more computer software modules are also configured to direct the one or more processors to perform forward projection on the re-mapped image volume to provide forward projection data. Also, the one or more computer software modules are configured to direct the one or more processors to provide an error projection based on the forward projection data. Further, the one or more computer software modules are also configured to direct the one or more processors to filter at least one of the initial reconstruction image, the re-mapped image volume provided by performing the material characterization of the image volume, wherein the filtering the re-mapped image volume is performed before performing the forward projection, the forward projection data provided by performing the forward projection on the re-mapped image volume, wherein the filtering the forward projection data is performed before applying the correction, or the error projection. The one or more computer software modules are also configured to direct the one or more processors to use the error projection to update the initial reconstruction image to provide an updated reconstruction image.

In another embodiment, an imaging system includes an acquisition unit and a processing unit. The acquisition unit includes a computed tomography (CT) detector configured to collect imaging data of an object to be imaged. The processing unit is operably coupled to the acquisition unit and configured to reconstruct the acquired imaging data into an initial reconstruction image. The processing unit is also configured to perform material characterization of an image volume of the initial reconstruction image to provide a re-mapped image volume from the initial reconstruction image, and to perform forward projection on the re-mapped image volume to provide forward projection data. Also the processing unit is configured to provide an error projection based on the forward projection data. Further, the processing unit is configured to filter at least one of the initial reconstruction image, the re-mapped image volume provided by performing the material characterization of the image volume, wherein the filtering the re-mapped image volume is performed before performing the forward projection, the forward projection data provided by performing the forward projection on the re-mapped image volume, wherein the filtering the forward projection data is performed before applying the correction, or the error projection. The processing unit is also configured to use the error projection to update the initial reconstruction image to provide an updated reconstruction image.

DETAILED DESCRIPTION OF THE INVENTION

Figure 1:
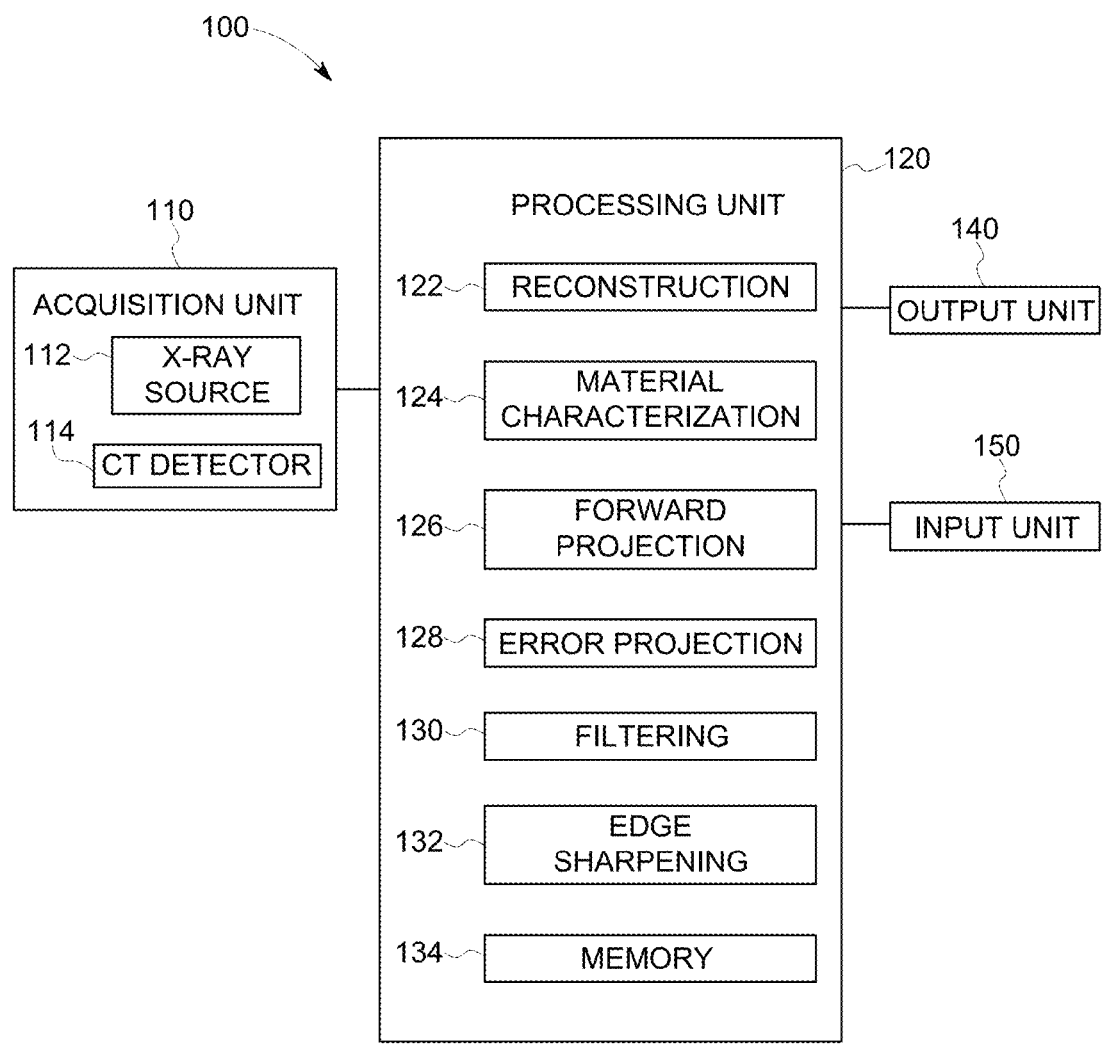
FIG. 1 is a schematic block diagram illustrating an imaging system in accordance with various embodiments.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. For example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and preceded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide systems and methods for filtering of data acquired by or associated with computed tomography (CT). Various embodiments employ one or more filtering schemes or techniques to address artifacts that may appear during or associated with multi-pass reconstruction techniques used in the reconstruction of CT imaging information, such as multi-material correction (MMC). As used herein, multi-pass reconstruction includes reconstruction techniques that include an initial reconstruction, include a subsequent forward projection after the initial reconstruction, and include an additional reconstruction after the forward projection. Additional processing steps may also be provided as part of a multi-pass reconstruction. Various filtering schemes or techniques disclosed herein may address artifacts without increasing or substantially increasing memory or computational time and/or capacity requirements. While certain examples discussed herein generally relate to MMC reconstruction techniques, it may be noted that the general principles may be applied to other multi-pass image generation or reconstruction techniques, including, for example, metal artifact reduction (MAR) and iterative reconstruction.

Generally, MMC-type spectral reconstruction in CT may be understood as a multi-pass technique including a number of steps. For example, in MMC reconstruction, a set of intermediate (or first-pass) CT images may be reconstructed from measured projection data or imaging data, and then used for material characterization. Material characterization may include, for example, material segmentation and decomposition. Forward projection may be utilized to generate or provide a system spectral model. A correction term may be calculated, for example to estimate and remove or address beam hardening using the spectral model. Next, final CT images may be reconstructed. In some embodiments, iterative corrections may also be applied. Accordingly, in various embodiments, advanced spectral correction for CT imaging may include one or more of the following steps: 1) Initial image reconstruction; 2) Material characterization; 3) Forward projection; 4) Correction term calculation; and 5) Projection update. For additional details regarding MMC, see U.S. patent application Ser. No. 13/677,010, U.S. Publication No. 2014/0133719, entitled "System And Method For Multi-Material Correction Of Image Data," filed Nov. 14, 2012 ("the 010 Application"), which is incorporated herein by reference in its entirety.

As disclosed herein, various methods or techniques of applying filtering to a MMC (or other multi-pass) reconstruction process may be utilized in various embodiments. For example, in a first approach, the initial CT images (formed as part of the initial image reconstruction process) may be filtered. As another example, in a second approach, the CT images formed after material characterization may be filtered. As yet another example, in a third approach, the forward projection may be filtered. As still one more example, in a fourth approach, filtering may be applied after calculating the correction term (or otherwise providing an error projection). It may be noted that, in some embodiments, two or more of the approaches may be combined.

Initial investigation indicates that the third approach, filtering the forward projection, provides a relatively high level of performance in removing or reducing artifacts such as undershoot or jagged edges. The filter, for example, may be a low pass filter configured to remove high frequency information. In some embodiments, the application of a filter after a forward projection may be expressed as $P_{io} = CONV(P_{io}, h)$, where $P_{io}$ is the forward projection, h is a filter, and "CONV" denotes a convolution or filtering process. It may be noted that, theoretically, as a forward projection, $P_{io}$ may be understood as three-dimensional (3D) data (e.g., detector column×detector×view angle). In various embodiments, h may be a one-dimensional (1D), two-dimensional (2D), or 3D filter. In some embodiments, to reduce computational time or capacity requirements while still addressing artifacts, h may be configured as a 1D filter along the detector column.

In various embodiments, different types of filters may be employed. By way of illustration, boxcar and/or Gaussian filters may be utilized. Different lengths of filters may be used. For example, a length of filter may be selected, modified, designed, or otherwise tuned for a particular application or type of application.

Optionally, in some embodiments, edge sharpening after filtering may be applied to improve image quality. For example, conventional edge sharpening techniques may be used. In some embodiments, a de-convolution method may be applied to sharpen edges, with the parameters for the de-convolution tuned empirically. As another example, the measured projection or imaging data (which includes the high frequency information lost during initial reconstruction, forward projection, and/or filtering) may be used as part of edge sharpening. For example, in some embodiments, edge sharpening may be provided to a filtered forward projection using the expression $P_{iof} = (P_t * g1) - ((P_t - P_{iof}) * g2)$, where $P_{iof}$ is the forward projection after filtering, $P_t$ is the measured total projection, and g1 and g2 denote image processing operations. In some embodiments, a "central-slice theorem" may be employed, in which the $P_t$ and $(P_t - P_{iof})$ terms are transformed into the Fourier domain, and a frequency blending technique is applied to recover or sharpen edges of $P_{iof}$.

Various embodiments provide improved imaging. A technical effect of at least one embodiment includes improved imaging, for example by reducing effects of artifacts. A technical effect of at least one embodiment includes reducing or eliminating the effect of jagged edge artifacts, for example artifacts caused by metallic objects. A technical effect of at least one embodiment includes reducing or eliminating the effect of undershoot. A technical effect of at least one embodiment is to reduce noise in images. A technical effect of at least one embodiment includes reducing or eliminating bone induced spectral (BIS) artifacts, which may be caused by variation among detector pixels coupled to spectral changes attenuated by bone, for example. A technical effect of at least one embodiment includes improved material identification or characterization in CT imaging.

FIG. 1 illustrates an imaging system 100 in accordance with an embodiment. The imaging system 100 may be configured, for example, to perform computed tomography (CT) scanning of an object, such as human or animal patient (or portion thereof). The imaging system 100 includes an acquisition unit 110 and a processing unit 120. Generally, the acquisition unit 110 is configured to acquire projection data or imaging data (e.g., CT data), and the processing unit 120 is configured to reconstruct images using the data acquired by the acquisition unit 110. It may be noted that various embodiments may include additional components, or may not include all of the components shown in FIG. 1 (for example, various embodiments may provide sub-systems for use with other sub-systems to provide an imaging system). Further, it may be noted that certain aspects of the imaging system 100 shown as separate blocks in FIG. 1 may be incorporated into a single physical entity, and/or aspects shown as a single block in FIG. 1 may be shared or divided among two or more physical entities.

The depicted acquisition unit 110 is configured as a CT acquisition unit, and includes a X-ray source 112 and a CT detector 114. (For additional information regarding example CT systems, see FIG. 9 and related discussion herein; see also FIG. 1 and related discussion of the 010 application.) The X-ray source 112 and the CT detector 114 (along with associated components such as bowtie filters, source collimators, detector collimators, or the like (not shown in FIG. 1)) may rotate about a central axis of a bore of a gantry (not shown in FIG. 1) of the system 100.

Generally, X-rays from the X-ray source 112 may be guided to an object to be imaged through a source collimator and bowtie filter. The object to be imaged, for example, may be a human patient, or a portion thereof (e.g., head or torso, among others). The source collimator may be configured to allow X-rays within a desired field of view (FOV) to pass through to the object to be imaged while blocking other X-rays. The bowtie filter module may be configured to absorb radiation from the X-ray source 112 to control distribution of X-rays passed to the object to be imaged.

X-rays that pass through the object to be imaged are attenuated by the object and received by the CT detector 114 (which may have a detector collimator associated therewith), which detects the attenuated X-rays and provides imaging information to the processing unit 120. The processing unit 120 may then reconstruct an image of the scanned portion of the object using the imaging information (or projection information) provided by the CT detector 114. The processing unit 120 may include or be operably coupled to the output unit 140, which in the illustrated embodiment is configured to display an image, for example, an image reconstructed by the processing unit 120 using imaging information from the CT detector 114. The depicted input unit 150 is configured to obtain input corresponding to a scan to be performed, with the processing unit 120 using the input to determine one or more aspects of filtering to be utilized during image reconstruction (e.g., type of filter, filtering parameters such as length, stage(s) at which to apply filtering, or the like). For example, the input unit 150 may include a keyboard, mouse, touchscreen or the like to receive input from an operator, and/or may include a port or other connectivity device to receive input from a computer or other source.

In the illustrated embodiment, the X-ray source 112 is configured to rotate about the object. For example, the X-ray source 112 and the CT detector 114 may be positioned about a gantry bore and rotated about the object. As the X-ray source 112 rotates about the object during an imaging scan, X-rays received by the CT detector 114 during one complete rotation provide a 360 degree view of X-rays that have passed through the object. Other scanning ranges may be used in alternative embodiments. It may also be noted that an individual scout scan may be performed from a single orientation.

As indicated herein, the processing unit 120 is configured to reconstruct an image using information obtained via the acquisition unit 110. For example, the processing unit 120 may be configured to employ MMC and/or other multi-pass reconstruction techniques, with filtering after one or more steps of a MMC or other multi-pass process.

The depicted processing unit 120 is operably coupled to the input unit 150, the output unit 140, and the acquisition unit 110. The processing unit 120, for example, may receive information regarding a scan from the input unit 150 that may be utilized in determining or tuning a filter to be applied during reconstruction. As another example, the processing unit 120 may receive imaging data or projection data from the CT detector 114. As one more example, the processing unit 120 may provide control signals to one or more aspects of the acquisition unit 110, such as the X-ray source 112. The processing unit 120 may include processing circuitry configured to perform one or more tasks, functions, or steps discussed herein.

In the illustrated embodiment, the processing unit includes a reconstruction module 122, a material characterization module 124, a forward projection module 126, an error projection module 128, a filtering module 130, an edge sharpening module 132, and a memory 134. It may be noted that other types, numbers, or combinations of modules may be employed in alternate embodiments, and/or various aspects of modules described herein may be utilized in connection with different modules additionally or alternatively. Generally, the reconstruction module 122, material characterization module 124, forward projection module 126, and error projection module 128 may perform MMC reconstruction, or other multi-pass reconstruction. For example, the reconstruction module 122, material characterization module 124, forward projection module 126, and error projection module 128 may, individually or in conjunction with other modules, perform one or more aspects of the methods, steps, or processes depicted in FIGS. 2-4 and related discussion of the 010 application.

The depicted reconstruction module 122 is configured to reconstruct an initial image using imaging or projection data acquired from the CT detector 114. Further, the reconstruction module 122 may be configured to reconstruct a subsequent image (e.g., final image) using information from one or more of the error projection module 128, the filtering module 130, or the edge sharpening module 132.

In the illustrated embodiment, the material characterization module 124 is configured to obtain or receive the initial reconstruction image from the reconstruction module 122 (and/or to receive a filtered initial reconstruction image from the filtering module 130). The depicted material characterization module 124 is configured to perform material characterization of an image volume of the initial reconstruction image (which may or may not have been filtered) to provide a re-mapped image volume from the initial reconstruction image.

The forward projection module 126 is configured to obtain or receive the re-mapped image volume from the material characterization module 124 (and/or to receive a filtered re-mapped image volume from the filtering module 130), and to perform forward projection on the re-mapped image volume to provide forward projection data. For example, in some embodiments, the forward projection module 126 may be configured to perform a forward projection on the re-mapped image volume (which may or may not have been filtered) to provide a material-based projection. The forward projection module 126 may be understood as receiving information in an image domain and providing a projection in a projection domain.

The error projection module 128 is configured to obtain or receive the forward projection data (e.g., a material-based projection) from the forward projection module 126 (and/or to receive a filtered forward projection from the filtering module 130), and to provide an error projection based on the forward projection data. For example, in some embodiments, the error projection module 128 may apply a correction to a material-based projection (which may or may not have been filtered) to update the material-based projection to provide an updated material-based projection. The correction applied may include a correction configured to address beam hardening.

The depicted filtering module 130 is configured to apply a filter to data or information from one or more steps of the multi-pass reconstruction (e.g., MMC reconstruction) process performed by one or more aspects of the processing unit 120. The filter may be a low-pass filter configured to remove high frequency information. Various different types of filters may be employed in different embodiments. For example, in some embodiments, a boxcar filter may be employed. The boxcar filter may have a configuration that may be expressed as [0.2 0.2 0.2 0.2 0.2]. As another example, a Gaussian filter may be employed. The Gaussian filter may have a configuration that may be expressed as [0.1 0.24 0.32 0.24 0.1]. The above examples are provided by way of illustration and not limitation; other types of filters or filter configurations may be employed in various embodiments.

In some embodiments, the type or configuration of filter employed may be varied or selected based on input received via the input unit 150. For example, a filter configuration may be selected or determined based on a portion of a human body to be imaged. The filter configuration may specify a filter length and/or other filter parameter, may specify a type of filter (e.g., boxcar, Gaussian), and/or may specify a stage of filtering (e.g., after material characterization and before forward projection; after forward projection and before applying a correction to address beam hardening). In some embodiments, a filter configuration having a first length may be selected when an image of a patient's head is to be reconstructed, while a filter configuration having a second length may be selected when a torso of a patient is to be reconstructed. As another example, a filter configuration (e.g., a stage at which filtering is to be performed) may be selected based on an artifact (e.g., jagged edge, BIS artifact, undershoot) to be addressed. The filter may be, for example a 2D filter (e.g., when filtering in the image domain), or a 1D filter (e.g., when filtering in the projection domain). As examples of filter determinations, a given filter configuration may be determined or selected based on a finite group of available filter configurations, may be tuned or adjusted from available or template filter configurations, or may be developed for a particular application. Further still, in some embodiments, the filtering module 130 may selectively activate or de-activate filtering depending on imaging requirements. For example, for a given scan which will not contain metallic implants, and for which a relatively high image quality is not required, filtering may be de-activated and not applied as part of a MMC process, while filtering may be activated or employed for other scans (e.g., scans including metallic bodies, or scans having higher image quality requirements, among others).

The filtering module 130 may apply a filter after one or more steps or sub-steps of a multi-pass reconstruction process (e.g., a MMC process). For example, the filtering module 130 may receive the initial reconstruction image from the reconstruction module 122, filter the initial reconstruction image, and provide the filtered initial reconstruction image to the material characterization module 124. As another example, the filtering module 130 may receive the re-mapped image volume provided by the material characterization module 124, filter the re-mapped image volume, and provide the filtered re-mapped image volume to the forward projection module 126 for forward projection of the filtered re-mapped image volume. As yet another example, the filtering module 130 may receive the forward projection data provided by the forward projection from the forward projection module 126, filter the forward projection data, and provide the filtered forward projection data to the error projection module 128. As one more example, the filtering module 130 may receive the error projection (e.g., an updated material-based projection) from the error projection module 128, filter the error projection, and provide the filtered error projection to the reconstruction 122 for reconstruction of an updated (e.g., final) image.

It may be noted that, while filtering may be applied at two or more stages (e.g., at two or more of the stages discussed above), it may be desirable to limit the application of filtering to application at a single stage to reduce computational requirements for applying the data filters. Initial investigation indicates that applying filtering after material characterization (and before forward projection) may be more beneficial than applying filtering before material characterization. Further, initial investigation indicates that applying filtering after the forward projection (and before applying the correction term) may be more beneficial than applying filtering after applying the correction term, and may be the most beneficial stage at which to apply filtering. Filtering before forward projection (e.g., before material characterization or after material characterization) may be understood as being performed in an image domain, and may require a 2D filter. Filtering after forward projection (e.g., after forward projection or after application of a correction term) may be understood as being performed in a projection domain. While filtering in the projection domain may be performed using a 2D or a 3D filter, a 1D filter may be employed to reduce computational requirements. Filtering in the projection domain thus may be more advantageous, in some embodiments, than filtering in the image domain, for example due to the use of a 1D filter that may reduce computational requirements.

Figure 2:
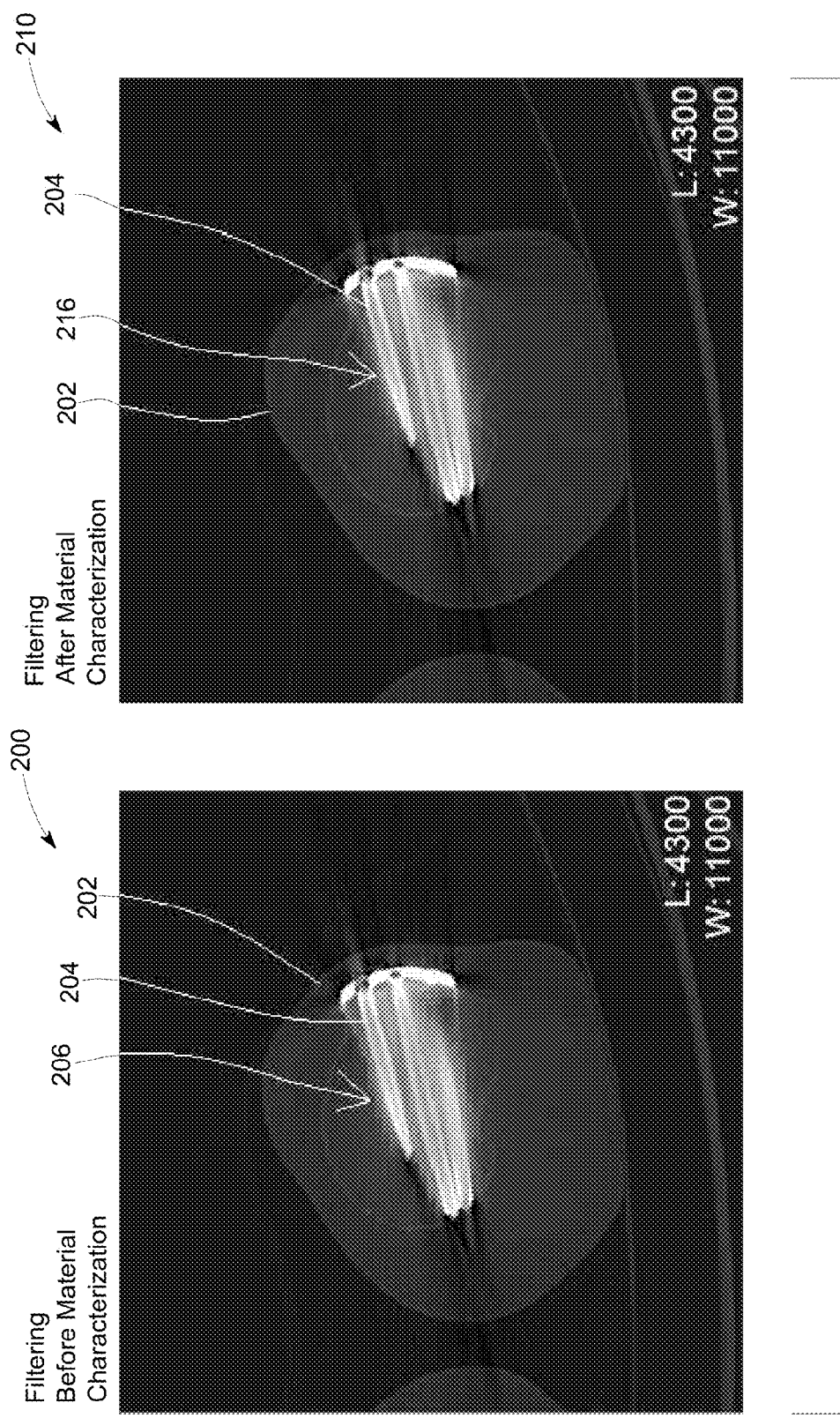
FIG. 2 provides a comparison of images obtained using MMC reconstruction with filtering in the image domain in accordance with various embodiments.

FIG. 2 provides a comparison of images obtained using MMC reconstruction with filtering in the image domain. The images of FIG. 2 correspond to an image of a spine 202 having a metallic implant 204. The image 200 (on the left side of FIG. 2) was obtained using filtering before material characterization, while the image 210 (on the right side of FIG. 2) was obtained using filtering after material characterization (but before forward projection). As seen in FIG. 2, the image 200 obtained using filtering before material characterization includes jagged artifact 206 induced by the metallic implant 204. However, the image 210 includes a region 216 having reduced jagged edges relative to the image 200. As seen in FIG. 2, filtering after material characterization may be more effective at addressing jagged edge artifacts (e.g., artifacts due to metallic bodies in a FOV) than filtering before material characterization. Accordingly, in some embodiments, when a jagged edge artifact is to be addressed (e.g., when it is known that a metal body (or bodies) will be within a FOV to be reconstructed), filtering after material characterization may be preferentially selected over filtering before material characterization. (It may be noted that the examples of preferential selection discussed herein are provided by way of illustration, and that, in various embodiments, other considerations in a given application may be considered alternatively or additionally. For example, a preferential selection discussed herein may be the sole basis of selecting a filter in some embodiments, while a preferential selection may provide a weighted factor to be considered along with other factors in selecting a filter configuration in other embodiments.)

Figure 3:
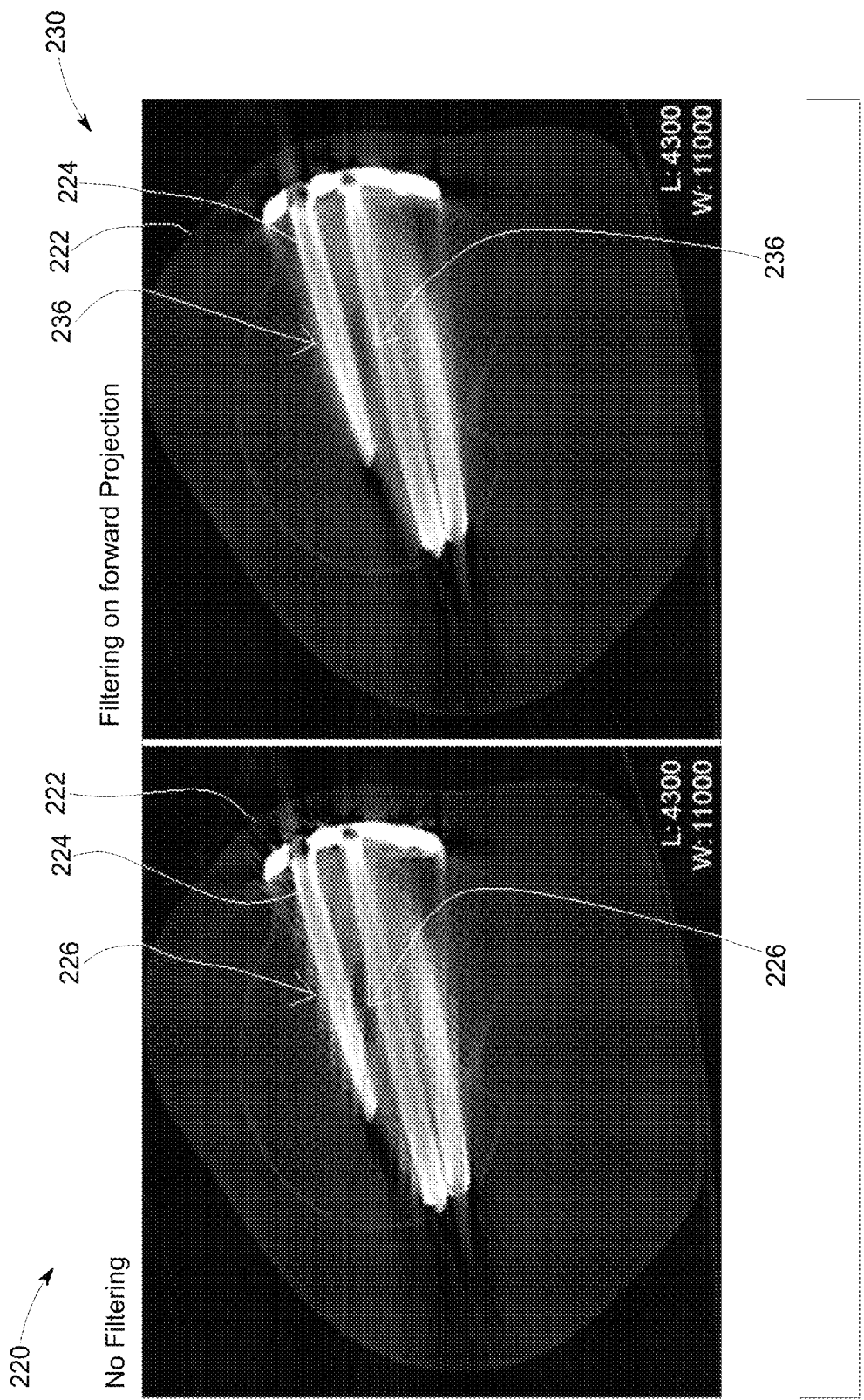
FIG. 3 provides a comparison of images obtained using MMC reconstruction, one without filtering, and one with filtering after the forward projection, in accordance with various embodiments.

Filtering after forward projection and before application of a correction term (e.g., a correction term addressing beam hardening) or otherwise providing an error projection may also provide improved imaging. For example, FIG. 3 provides a comparison of images obtained using MMC reconstruction, one without filtering, and one with filtering after the forward projection (e.g., filtering the material-based projection provided by performing a forward projection on the re-mapped image volume). The images of FIG. 3 correspond to an image of a spine 222 having a metallic implant 224. The image 220 (on the left side of FIG. 3) was obtained without filtering during a MMC reconstruction, while the image 230 (on the right side of FIG. 3) was obtained using filtering after forward projection (but before applying a correction term). As seen in FIG. 3, the image 220 obtained without filtering includes jagged artifacts 226 induced by the metallic implant 224. However, the image 230 includes regions 236 having eliminated or reduced jagged edges relative to the image 220. As seen in FIG. 3, filtering after forward projection may be effective at addressing jagged edge artifacts (e.g., artifacts due to metallic bodies in a FOV). Accordingly, in some embodiments, when a jagged edge artifact is to be addressed (e.g., when it is known that a metal body (or bodies) will be within a FOV to be reconstructed), filtering after forward projection may be preferentially selected over one or more other filtering approaches.

Figure 4:
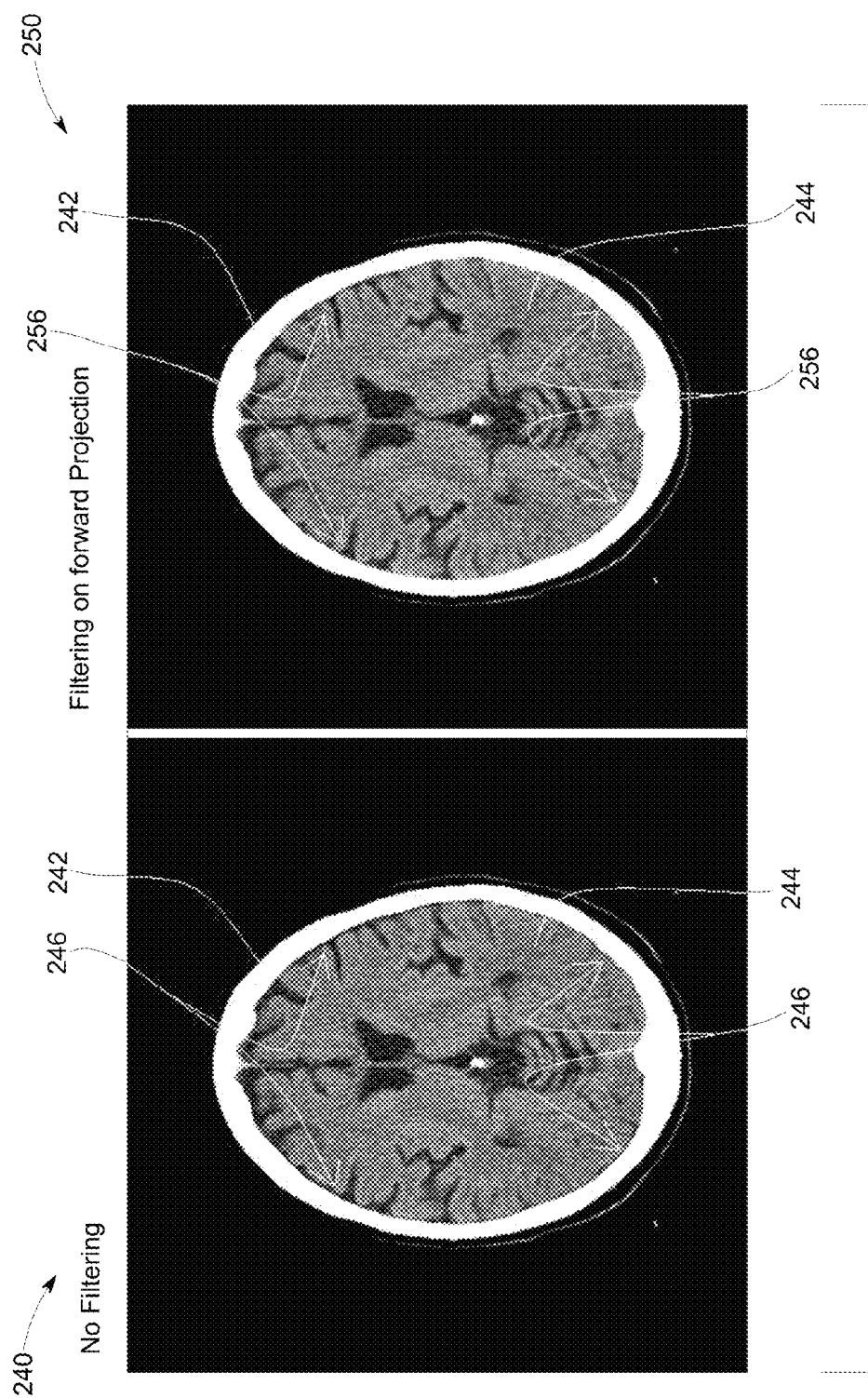
FIG. 4 provides a comparison of images of a brain obtained using MMC reconstruction, one without filtering, and one with filtering after the forward projection, in accordance with various embodiments.

FIG. 4 provides a comparison of images obtained using MMC reconstruction, one without filtering, and one with filtering after the forward projection (e.g., filtering the material-based projection provided by performing a forward projection on the re-mapped image volume). The images of FIG. 4 correspond to an image of a skull 242 and a brain 244. Images of the skull and brain include a bone/brain interface that may be subject to undershoot artifacts. The image 240 (on the left side of FIG. 4) was obtained without filtering in a MMC reconstruction, while the image 250 (on the right side of FIG. 4) was obtained using filtering after forward projection (but before applying a correction term). As seen in FIG. 4, the image 240 obtained without filtering includes relatively larger undershoot regions 246. However, the image 250 includes relatively smaller undershoot regions 256 having reduced size relative to the undershoot regions 246 of the image 240. As seen in FIG. 4, filtering after forward projection may be effective at addressing undershoot (e.g., undershoot of a bone/brain interface). Accordingly, in some embodiments, when undershoot is anticipated (e.g., when a brain scan is performed), filtering after forward projection may be preferentially selected over one or more other filtering approaches.

Figure 5:
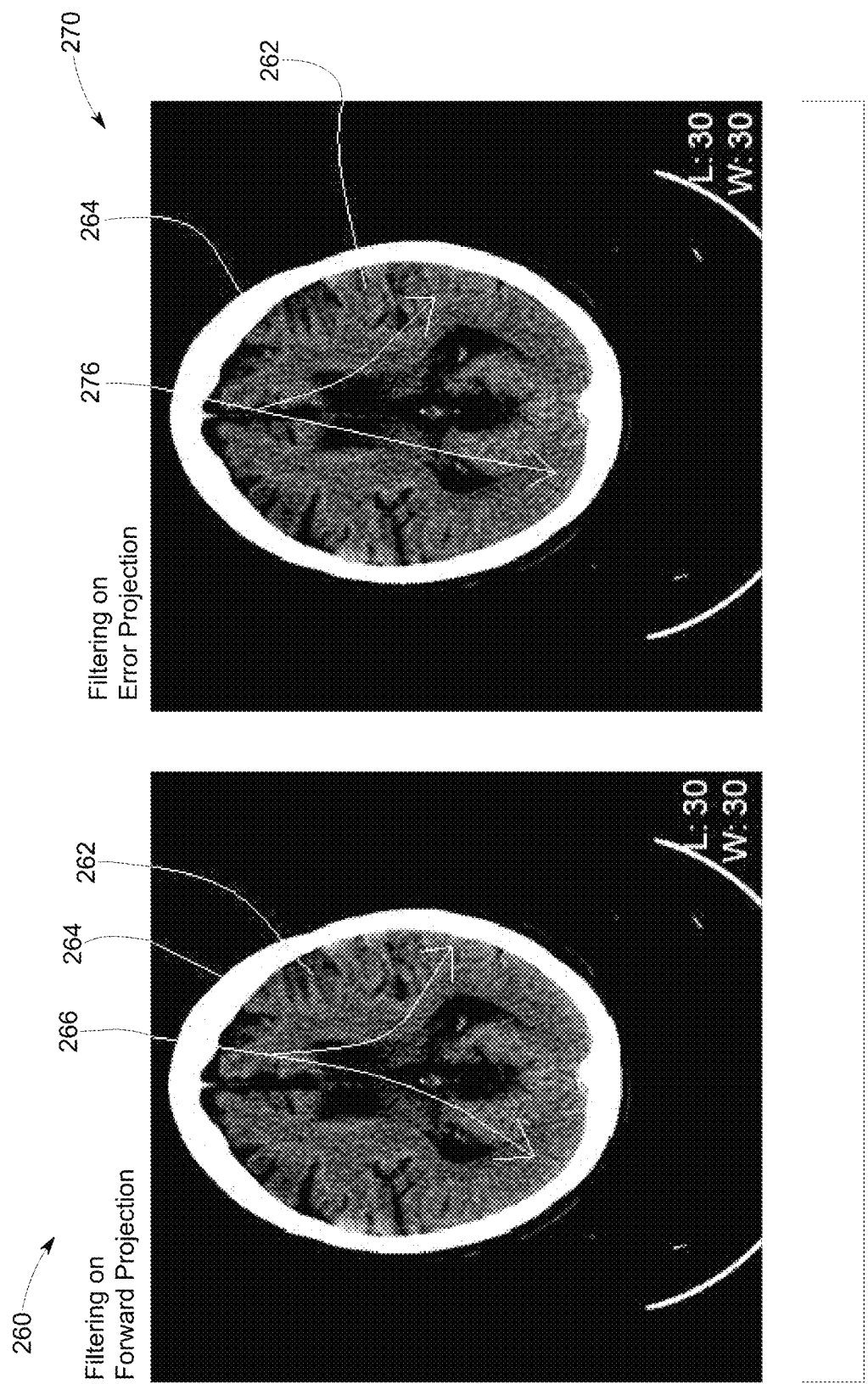
FIG. 5 provides a comparison of images obtained using MMC reconstruction with filtering in the projection domain in accordance with various embodiments.

FIG. 5 provides a comparison of images obtained using MMC reconstruction with filtering in the projection domain. The images of FIG. 5 correspond to an image of a brain 262 and a skull 264. The image 260 (on the left side of FIG. 5) was obtained using filtering after forward projection (but before error projection (e.g., applying a correction term addressing beam hardening)), while the image 270 (on the right side of FIG. 5) was obtained using filtering after error projection. As seen in FIG. 5, the image 270 obtained using filtering after the correction term includes ringed or smudged areas 276. The ringed or smudged areas may be caused by BIS artifacts. However, the image 260 includes regions 266 having no rings or smudges, or reduced ringing or smudging relative to the image 270. As seen in FIG. 5, filtering after forward projection (and before error projection) may be more effective at addressing BIS artifacts (e.g., artifacts due to variation in detector components such as pixels) than filtering after error projection (e.g., after applying a correction term). Accordingly, in some embodiments, when BIS artifacts are anticipated, filtering after forward projection may be preferentially selected over filtering after error projection.

It may be noted that the particular form of the filter may vary by application and/or stage at which the filter is applied. For example, in some embodiments, a filter that may be utilized after forward projection (and before application of the correction term) may be expressed as $P_{io}$=CONV($P_{io}$, h), where $P_{io}$ is the forward projection, h is a filter or filter kernel, and "CONV" denotes a convolution or filtering process. It may be noted that, theoretically, as a forward projection, $P_{io}$ may be understood as three-dimensional (3D) data (e.g., detector column×detector×view angle). In various embodiments, h may be a 1D, 2D, or 3D filter. For example, a 1D filter may be employed along the detector column of a forward projection. In various embodiments, different types of filters may be used for different applications, such as imaging of different body parts. It may be noted that one or more parameters of a filter may be varied responsive to the type of scan or imaging to be performed. For example, different lengths of filter may be used for different types of imaging, such as a first length for filtering imaging data corresponding to head scan, and a second, different length for filtering imaging data corresponding to a body scan. Further, in some embodiments, adaptive filtering schemes may be applied to different regions of interest. For example, an image may have a number of regions, with different regions filtered differently. In one example scenario, a region associated with a metallic body may be filtered while a region not associated with the metallic object may not be filtered. In another example scenario, a first region associated with a bone/brain interface may be filtered using a first filter configuration, a second region associated with a metallic body may be filtered using a second filter configuration, and a third region may not be filtered.

Returning to FIG. 1, the depicted edge sharpening module 132 is configured to edge-sharpen at least one of the forward projection data (e.g., material-based projection or the error projection (e.g., updated material-based projection). The edge sharpening module 132 may receive information from, for example, one or more of the filtering module 130, the error projection module 128, or the CT detector 114, to be used in edge sharpening. For example, filtering of the forward projection data may be performed after forward projection. In some embodiments, the forward projection data, after filtering, may be edge-sharpened. In some embodiments, the forward projection data may be provided to the error projection module 128, and an error projection provided based on the forward projection data (e.g., a correction term may be applied to provide an updated material-based projection), with the error projection provided to the edge sharpening module 132 for edge sharpening.

Figure 6:
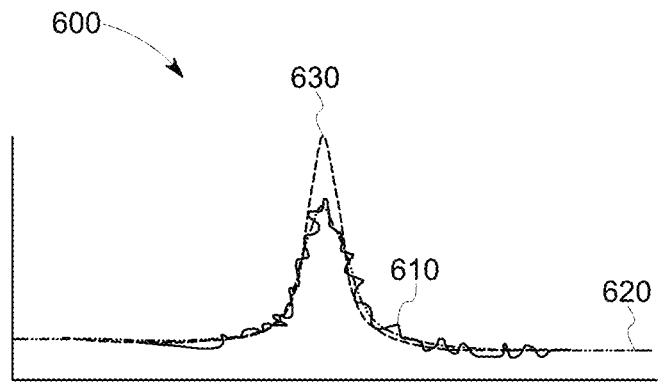
FIG. 6 illustrates an example of edge sharpening in accordance with an embodiment.

In various embodiments, different edge sharpening techniques may be applied. For example, a de-convolution method may be applied to sharpen an edge. FIG. 6 illustrates an example of edge sharpening. In FIG. 6, a graph 600 includes a vertical axis corresponding to signal intensity and a horizontal axis corresponding to detector row. A first signal 610 from a raw (e.g., unfiltered forward projection) is shown, having a wavy or irregular contour. A second signal 620 is provided by filtering the forward projection. As shown in FIG. 6, the second signal 620 is substantially smoother or more continuous than the first signal 610. However, during the initial reconstruction, projection, and/or filtering process, high frequency information that may be useful in defining, for example, edges or boundaries in an image, may be removed. Edge-sharpening may be performed to improve image quality. As seen in FIG. 6, a third signal 630 may be provided by edge-sharpening the second signal 620 (e.g., the filtered signal), providing a sharpened edge relative to the second signal 620. For example, conventional edge sharpening techniques may be used. A de-convolution method may be applied to sharpen edges (e.g., to provide the third signal 630). The parameters used for the de-convolution may be developed or tuned empirically.

Figure 7:
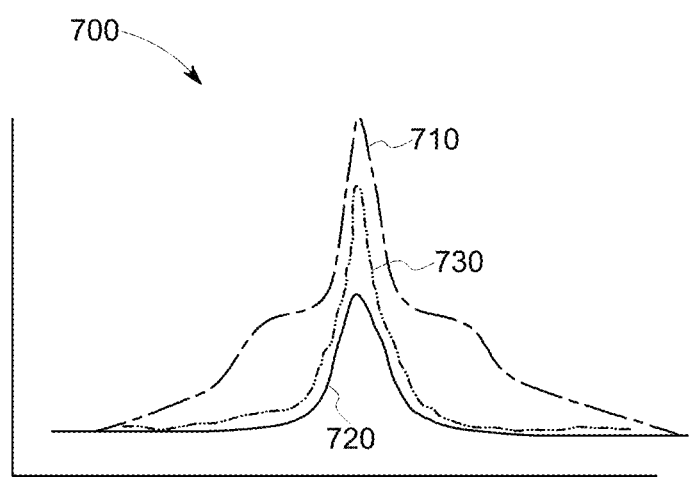
FIG. 7 illustrates an example of edge sharpening in accordance with an embodiment.

As another example of an edge sharpening technique employed in some embodiments, the measured projection or imaging data (which includes the high frequency information lost during initial reconstruction, forward projection, and/or filtering) may be used as part of edge sharpening. FIG. 7 illustrates an example of edge sharpening on a graph 700. The graph 700 includes a vertical axis corresponding to signal intensity and a horizontal axis corresponding to detector row. A first signal 710 is shown from measured projection or imaging data (e.g., data from the CT detector 114). The measured projection or imaging data may be used for initial image reconstruction, as well as for edge sharpening. A second signal 720 is provided by filtering the forward projection. As shown in FIG. 7, the second signal 720 is substantially smoother or more continuous than the first signal 710. However, the second signal 720 may not provide a desired sharpness of edge. Edge-sharpening may be performed to improve image quality. The first signal 710 and the second signal 720 may be blended or otherwise combined to provide an edge-sharpened signal. As seen in FIG. 7, a third signal 730 may be provided by edge-sharpening the second signal 720 (e.g., the filtered signal), providing a sharpened edge relative to the second signal 720. For example, in some embodiments, edge sharpening may be provided to a filtered forward projection using the expression $P_{iof}=(P_t*g1)-((P_t-P_{iof})*g2)$, where $P_{iof}$ is the forward projection after filtering, $P_t$ is the measured total projection, and g1 and g2 denote image processing operations. In some embodiments, a "central-slice theorem" may be employed, in which the $P_t$ and ($P_t-P_{iof}$) terms are transformed into the Fourier domain, and a frequency blending technique is applied to recover or sharpen edges of $P_{iof}$.

Returning to FIG. 1, the input unit 150 may be configured to obtain an input that corresponds to one or more settings or characteristics of a scan to be performed, and to provide the input (or information corresponding to the input) to the processing unit 120, which may use the input to determine, adjust, or select a filter configuration to be used to filter data during a multi-pass reconstruction. The input may include, for example, a portion of the body to be scanned (e.g., head, body). The input may include an expected artifact (e.g., jagged edge, BIS, undershoot), or information from which an expected artifact may be determined to be expected or anticipated. For example, if the scan includes a metallic object, a jagged edge artifact may be expected and addressed or accounted for in filter configuration. As another example, if a head or brain scan is to be performed, an undershoot artifact may be expected and addressed or accounted for in filter configuration. As one more example, if a bone scan is to be performed using a pixelated detector, a BIS artifact may be expected and addressed or accounted for in filter configuration. The input unit 150 may be configured to accept a manual user input, such as via a touchscreen, keyboard, mouse, or the like. Additionally or alternatively, the input unit 150 may receive information from another aspect of the imaging system 100, another system, or a remote computer, for example, via a port or other connectivity device. For example, a scout scan may be performed and a metallic object identified in the scout scan, with information provided to the input unit 150 indicating (and/or describing) the presence of the metallic object. The input unit 150 may also be configured to obtain user approval or denial of a proposed data filter configuration. As used herein, to "obtain" may include, for example, to receive.

The output unit 140 is configured to provide information to the user. The output unit 140 may be configured to display, for example, a scout image, an intermediate image (e.g., an initial reconstruction), or a final image. The output unit 140 may include one or more of a screen, a touchscreen, a printer, or the like.

Figure 8:
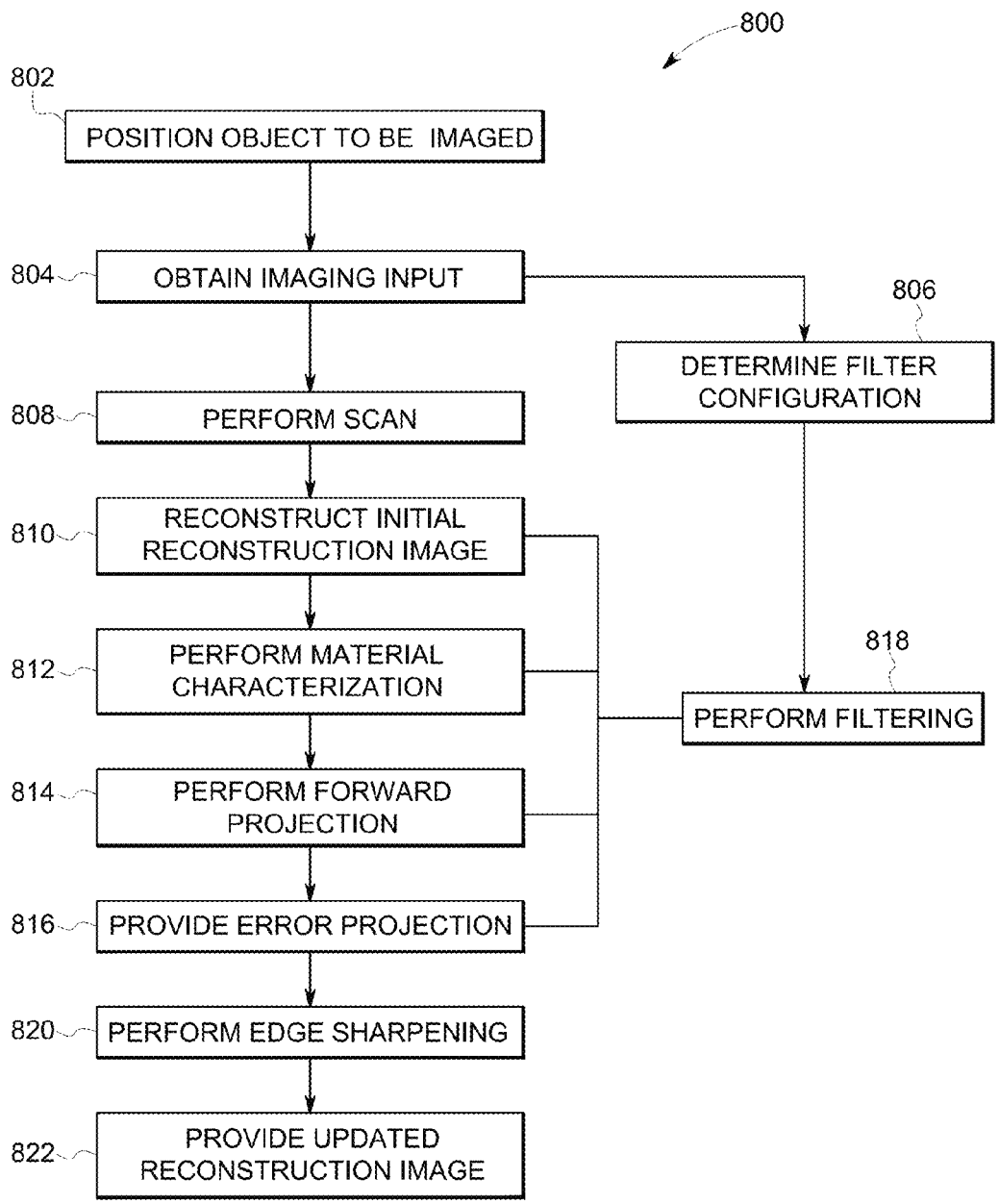
FIG. 8 is a flowchart of a method in accordance with an embodiment.

FIG. 8 provides a flowchart of a method 800 for imaging an object (e.g., obtaining a CT image of the object using MMC or other multi-pass technique). The method 800, for example, may employ or be performed by structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 800 may be able to be used as one or more algorithms to direct hardware (e.g., one or more aspects of the processing unit 120) to perform one or more operations described herein.

At 802, an object to be imaged is positioned. For example, the object may be a human patient positioned on a table in a bore of a CT imaging system.

At 804, imaging input is obtained. For example, the imaging input may include a user input that includes a scan technique or scanning operational parameters (e.g., tube voltage). The input may also include an identification of a body portion (e.g., head, body), and/or information describing or corresponding to one or more artifacts that may be expected (e.g., information describing or corresponding to presence of a metallic object that may cause jagged edge artifacts). The input may be utilized for example, to set scanning parameters, as well as parameters or settings used in reconstruction (e.g., data filter configurations or settings to be used as part of a MMC reconstruction process).

At 806, a filter configuration is determined. The filter configuration may be determined using information provided via the input (e.g., a user input) at 804. The determined filter configuration may define one or more of a type of filter, filter parameters, or a stage (or stages) of a multi-pass reconstruction process (e.g., MMC reconstruction) at which filtering is to be performed. For example, a filter configuration (e.g., a length of filter) may be determined or selected based upon a portion of a human patient to be imaged. As another example, a filter configuration may be determined or selected based on a type of artifact to be addressed. For instance, the stage (or stages) at which filtering is performed may be selected or determined based on a type of artifact to be addressed. In some embodiments, the filtering may be configured to be performed upon a material-based projection provided by forward projection of a re-mapped image volume when a BIS artifact is to be addressed. In some embodiments, the filtering may be configured to be performed after one or more of material characterization or forward projection when a jagged edge artifact (e.g., due to a metallic body) is to be addressed.

At 808, a scan is performed. The X-ray source and detector may be rotated about the object being imaged and operated in a manner prescribed by predetermined scanning parameters to collect imaging information at the detector. Imaging or projection data or information is obtained via the detector during the performance of the scan.

At 810, an initial reconstruction image is reconstructed (e.g., using reconstruction module 122 of processing unit 120). The initial reconstruction image is reconstructed based on imaging information acquired via the detector during an imaging scan.

At 812, material characterization is performed (e.g., using material characterization module 124 of processing unit 120). In the depicted embodiment, material characterization is performed of an image volume of the initial reconstruction image (the initial reconstruction image may be a filtered initial reconstruction image) to provide a re-mapped image volume from the initial reconstruction image. The image volume on which the material characterization is performed may include the entire initial reconstruction image or a portion thereof. The material characterization may be performed using a linear mapping in various embodiments. In some embodiments, the material characterization may be performed using a non-linear mapping.

At 814, forward projection is performed (e.g., using forward projection module 126 of processing unit 120). In the depicted embodiment, the forward projection is performed on the re-mapped image volume (the re-mapped image volume may be a filtered re-mapped image volume) to provide forward projection data. For example, the forward projection data in some embodiments may be a material-based projection. The re-mapped image volume may be understood as being in an image domain before the forward projection, while the forward projection data (e.g., material-based projection) provided at 814 may be understood as being in a projection domain.

At 816, an error projection is provided. In the depicted embodiment, the error projection is provided based on the forward projection data. For example, a correction may be applied (e.g., using correction unit 128 of processing unit 120) as part of providing the error projection. In some embodiments, the correction is applied to a material-based projection (the material-based projection may be a filtered material-based projection in some embodiments and an unfiltered material-based projection in other embodiments) to update the material-based projection to provide an updated material-based projection. The correction, for example, may be used to address beam hardening.

At 818, filtering is performed (e.g., using filtering module 130 of processing unit 120). The filtering may be performed using a low pass data filter to remove high frequency information. The filtering may be performed with a boxcar, Gaussian, or other type of filter. The filter may be a 2D filter (e.g., when filtering in the image domain), or may be a 1D filter (e.g., when filtering in the projection domain). In some embodiments, a 2D filter or 3D filter may be utilized when filtering in the projection domain. It may be noted that filtering, as seen in FIG. 8, may be performed after one or more steps of a multi-pass reconstruction technique such as MMC. For example, filtering may be performed after one or more of steps 810, 812, 814, or 816 depicted in FIG. 8. For example, as discussed herein, filtering may be performed between steps 812 and 814 (in an image domain), and/or between steps 814 and 816 (in a projection domain). In some embodiments, as discussed herein, filtering may be performed upon a material-based projection provided by performing the forward projection on the re-mapped image volume at 814 and before applying the correction at 816.

At 820, edge sharpening is performed (e.g., using edge sharpening module 132 of processing unit 120). In the depicted embodiment, edge sharpening is performed after filtering the material-based projection and after applying the correction term at 818. It may be noted that in other embodiments, edge sharpening may be performed after filtering the material-based projection but before applying the correction term at 818.

At 822, an updated reconstruction image is provided (e.g., using reconstruction module 122 or other aspect of processing unit 120). The updated reconstruction image may be provided using the error projection (e.g., updated material-based projection) generated at 816 (optionally, with filtering and/or edge sharpening as discussed herein). The updated reconstruction image may be a final image, or may be an intermediate image used for additional steps, passes, or iterations through a reconstruction process (e.g., the intermediate image may be considered as an initial reconstruction image for subsequent steps, passes, or iterations). Using the error projection to provide an updated reconstruction image may, in some embodiments, include correcting or applying measured projection data and providing a new reconstruction using the corrected measured projection data. In some embodiments, using the error projection to provide an updated reconstruction image may include providing a new reconstruction, and combining the new reconstruction with the initial reconstruction.

Various embodiments discussed or described herein provide for improved reconstruction of CT images using multi-pass reconstruction techniques, such as MMC. Various embodiments provided improved imaging with respect to undershoot, jagged edge artifacts, and/or BIS artifacts. Further, various embodiments provide for reduced noise in multi-pass reconstruction. Filtering may be performed at a particular stage with respect to a particular material. For example, in various embodiments, filtering on a forward projection of iodine efficiently provides improved imaging. Further, in some embodiments, edge sharpening may be utilized to provide further improved image quality.

Figure 9:
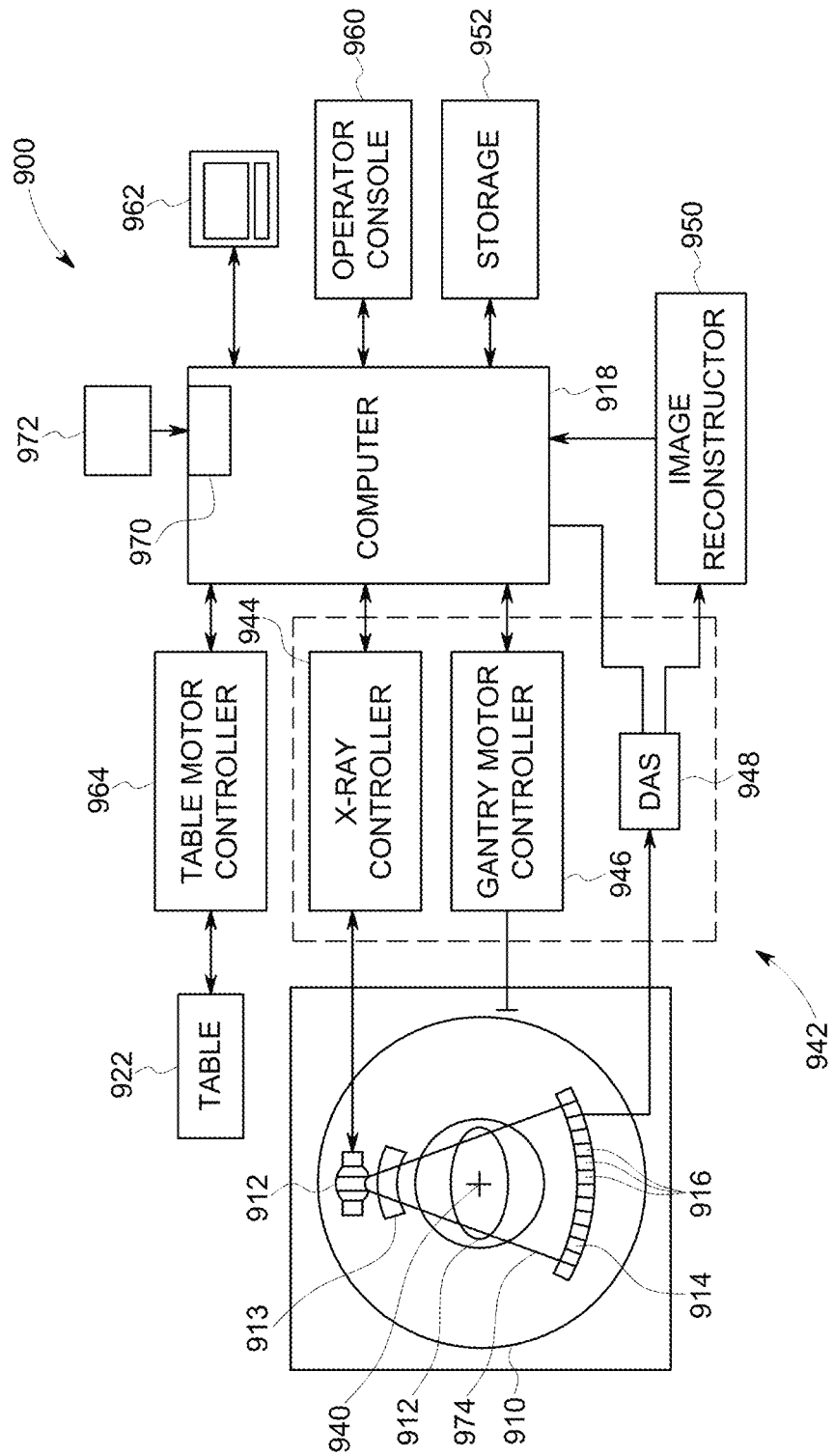
FIG. 9 is a schematic block diagram of a computed tomography (CT) imaging system in accordance with an embodiment.

Various methods and/or systems (and/or aspects thereof) described herein may be implemented using a medical imaging system. For example, FIG. 9 is a block schematic diagram of an exemplary CT imaging system 900 that may be utilized to implement various embodiments discussed herein. Although the CT imaging system 900 is illustrated as a standalone imaging system, it should be realized that the CT imaging system 900 may form part of a multi-modality imaging system. For example, the multi-modality imaging system may include the CT imaging system 900 and a positron emission tomography (PET) imaging system, or a single photon emission computed tomography (SPECT) imaging system. It should also be understood that other imaging systems capable of performing the functions described herein are contemplated as being used.

The CT imaging system 900 includes a gantry 910 that has the X-ray source 912 that projects a beam of X-rays toward the detector array 914 on the opposite side of the gantry 910. A source collimator 913 and a bowtie filter module 915 are provided proximate the X-ray source 912. The detector array 914 includes a plurality of detector elements 916 that are arranged in rows and channels that together sense the projected X-rays that pass through a subject 917. The imaging system 900 also includes a computer 918 that receives the projection data from the detector array 914 and processes the projection data to reconstruct an image of the subject 917. The computer 918, for example, may include one or more aspects of the processing unit 120, or be operably coupled to one or more aspects of the processing unit 120. In operation, operator supplied commands and parameters are used by the computer 918 to provide control signals and information to reposition a motorized table 922. More specifically, the motorized table 922 is utilized to move the subject 917 into and out of the gantry 910. Particularly, the table 922 moves at least a portion of the subject 917 through a gantry opening (not shown) that extends through the gantry 910. Further, the table 922 may be used to move the subject 917 vertically within the bore of the gantry 910.

As discussed above, the detector 914 includes a plurality of detector elements 916. Each detector element 916 produces an electrical signal, or output, that represents the intensity of an impinging X-ray beam and hence allows estimation of the attenuation of the beam as it passes through the subject 917. During a scan to acquire the X-ray projection data, the gantry 910 and the components mounted thereon rotate about a center of rotation 940. FIG. 9 shows only a single row of detector elements 916 (i.e., a detector row). However, the multislice detector array 914 includes a plurality of parallel detector rows of detector elements 916 such that projection data corresponding to a plurality of slices can be acquired simultaneously during a scan.

Rotation of the gantry 910 and the operation of the X-ray source 912 are governed by a control mechanism 942. The control mechanism 942 includes an X-ray controller 944 that provides power and timing signals to the X-ray source 912 and a gantry motor controller 946 that controls the rotational speed and position of the gantry 910. A data acquisition system (DAS) 948 in the control mechanism 942 samples analog data from detector elements 916 and converts the data to digital signals for subsequent processing. An image reconstructor 950 receives the sampled and digitized X-ray data from the DAS 948 and performs high-speed image reconstruction. The reconstructed images are input to the computer 918 that stores the image in a storage device 952. The computer 918 may also receive commands and scanning parameters from an operator via a console 960 that has a keyboard. An associated visual display unit 962 allows the operator to observe the reconstructed image and other data from computer. It may be noted that one or more of the computer 918, controllers, or the like may be incorporated as part of a processing unit such as the processing unit 160 discussed herein.

The operator supplied commands and parameters are used by the computer 918 to provide control signals and information to the DAS 948, the X-ray controller 944 and the gantry motor controller 946. In addition, the computer 918 operates a table motor controller 964 that controls the motorized table 922 to position the subject 917 in the gantry 910. Particularly, the table 922 moves at least a portion of the subject 917 through the gantry opening.

In various embodiments, the computer 918 includes a device 970, for example, a CD-ROM drive, DVD drive, magnetic optical disk (MOD) device, or any other digital device including a network connecting device such as an Ethernet device for reading instructions and/or data from a tangible non-transitory computer-readable medium 972, that excludes signals, such as a CD-ROM, a DVD or another digital source such as a network or the Internet, as well as yet to be developed digital means. In another embodiment, the computer 918 executes instructions stored in firmware (not shown). The computer 918 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

In the exemplary embodiment, the X-ray source 912 and the detector array 914 are rotated with the gantry 910 within the imaging plane and around the subject 917 to be imaged such that the angle at which an X-ray beam 974 intersects the subject 917 constantly changes. A group of X-ray attenuation measurements, i.e., projection data, from the detector array 914 at one gantry angle is referred to as a "view". A "scan" of the subject 917 comprises a set of views made at different gantry angles, or view angles, during one or more revolutions of the X-ray source 912 and the detector 914. In a CT scan, the projection data is processed to reconstruct an image that corresponds to a three-dimensional volume taken of the subject 917. It may be noted that, in some embodiments, an image may be reconstructed using less than a full revolution of data. For example, with a multi-source system, substantially less than a full rotation may be utilized. Thus, in some embodiments, a scan (or slab) corresponding to a 360 degree view may be obtained using less than a complete revolution.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. A method comprising:

acquiring imaging data of an object to be imaged from a computed tomography (CT) detector;
reconstructing, with at least one processing unit, the acquired imaging data into an initial reconstruction image;
performing, with the at least one processing unit, material characterization of an image volume of the initial reconstruction image to provide a re-mapped image volume from the initial reconstruction image;
performing, with the at least one processing unit, forward projection on the re-mapped image volume to provide forward projection data;
providing, with the at least one processing unit, an error projection based on the forward projection data;
filtering at least one of:
the initial reconstruction image before performing the material characterization,
the re-mapped image volume provided by performing the material characterization of the image volume, wherein the filtering the re-mapped image volume is performed before performing the forward projection,
the forward projection data provided by performing the forward projection on the re-mapped image volume, wherein the filtering the forward projection data is performed before providing the error projection, or
the error projection to provide a filtered error projection; and
correcting the forward projection data with the error projection to provide corrected projection data when the error projection is not filtered, correcting the forward projection with the filtered error projection to provide the corrected projection data when the error projection is filtered, and reconstructing an updated reconstruction image using the corrected projection data.

2. The method of claim 1, wherein
performing the forward projection comprises performing the forward projection on the re-mapped image volume to provide a material-based projection;
providing the error projection comprises applying, with the at least one processing unit, a correction to the material-based projection to update the material-based projection to provide an updated material-based projection; and
filtering comprises filtering at least one of:
the re-mapped image volume provided by performing the material characterization of the image volume, wherein the filtering the re-mapped image volume is performed before performing the forward projection; or
the material-based projection provided by performing the forward projection on the re-mapped image volume, wherein the filtering the material-based projection is performed before applying the correction.

3. The method of claim 1, wherein the object to be imaged is a portion of a human patient, the method further comprising selecting a type of filter from a group of available filters including at least a boxcar filter or a Gaussian filter based on a type of the portion of body to be imaged.

4. The method of claim 1, further comprising selecting a type of filter from a group of available filters including at least a boxcar filter and a Gaussian filter based on a type of artifact to be addressed.

5. The method of claim 1, further comprising selecting a stage at which to perform filtering from a group of stages including after material characterization, before forward projection, after forward projection, or before correcting beam hardening based on a type of artifact to be addressed.

6. The method of claim 5, further comprising selecting filtering the forward projection data based on a bone induced spectrum artifact to be addressed.

7. The method of claim 1, comprising filtering the re-mapped image volume using a 2D filter.

8. The method of claim 1, comprising filtering the forward projection data using a 1D filter.

9. The method of claim 1, comprising:
filtering the forward projection data; and
edge-sharpening, after filtering the forward projection data, at least one of the forward projection or the error projection.

10. A tangible and non-transitory computer readable medium comprising one or more computer software modules configured to direct one or more processors to:
acquire imaging data of an object to be imaged from a computed tomography (CT) detector;
reconstruct the acquired imaging data into an initial reconstruction image;
perform material characterization of an image volume of the initial reconstruction image to provide a re-mapped image volume from the initial reconstruction image;
perform forward projection on the re-mapped image volume to provide forward projection data;
provide an error projection based on the forward projection data;
filter at least one of:
the initial reconstruction image before performing the material characterization,
the re-mapped image volume provided by performing the material characterization of the image volume, wherein the filtering the re-mapped image volume is performed before performing the forward projection,
the forward projection data provided by performing the forward projection on the re-mapped image volume, wherein the filtering the forward projection data is performed before providing the error projection, or
the error projection to provide a filtered error projection; and
correct the forward projection data with the error projection to provide corrected projection data when the error projection is not filtered, correct the forward projection data with the filtered error projection to provide the corrected projection data when the error projection is filtered, and reconstruct an updated reconstruction image using the corrected projection data.

11. The tangible and non-transitory computer readable medium of claim 10, wherein the computer readable medium is further configured to direct the one or more processors to:
perform forward projection on the re-mapped image volume to provide a material-based projection;
provide the error projection by applying a correction to the material-based projection to update the material-based projection to provide an updated material-based projection; and
filter by filtering at least one of:
the re-mapped image volume provided by performing the material characterization of the image volume, wherein the filtering the re-mapped image volume is performed before performing the forward projection; or
the material-based projection provided by performing the forward projection on the re-mapped image volume, wherein the filtering the material-based projection is performed before applying the correction.

12. The tangible and non-transitory computer readable medium of claim 10, wherein the computer readable medium is further configured to direct the one or more processors to select a type of filter from a group of available filters including at least a boxcar filter or a Gaussian filter based on a type of a portion of a human body to be imaged.

13. The tangible and non-transitory computer readable medium of claim 10, wherein the computer readable medium is further configured to direct the one or more processors to select a type of filter from a group of available filters including at least a boxcar filter or a Gaussian filter based on a type of artifact to be addressed.

14. The tangible and non-transitory computer readable medium of claim 10, wherein the computer readable medium is further configured to direct the one or more processors to select a stage at which to perform filtering from a group of stages including after material characterization, before forward projection, after forward projection, or before correcting beam hardening determine a stage at which to perform filtering based on a type of artifact to be addressed.

15. The tangible and non-transitory computer readable medium of claim 10, wherein the computer readable medium is further configured to direct the one or more processors to filter the re-mapped image volume using a 2D filter.

16. The tangible and non-transitory computer readable medium of claim 10, wherein the computer readable medium is further configured to direct the one or more processors to filter the forward projection data using a 1D filter.

17. An imaging system comprising:
an acquisition unit comprising a computed tomography (CT) detector configured to collect imaging data of an object to be imaged; and
at least one processor operably coupled to the acquisition unit and configured to:
reconstruct the acquired imaging data into an initial reconstruction image;
perform material characterization of an image volume of the initial reconstruction image to provide a re-mapped image volume from the initial reconstruction image;
perform forward projection on the re-mapped image volume to provide forward projection data;
provide an error projection based on the forward projection data;
filter at least one of:
the initial reconstruction image before performing the material characterization,
the re-mapped image volume provided by performing the material characterization of the image volume, wherein the filtering the re-mapped image volume is performed before performing the forward projection,
the forward projection data provided by performing the forward projection on the re-mapped image volume, wherein the filtering the forward projection data is performed before providing the error projection, or
the error projection to provide a filtered error projection; and
correct the forward projection data with the error projection to provide corrected projection data when the error projection is not filtered, correct the forward projection data with the filtered error projection to provide the corrected projection data when the error projection is filtered, and reconstruct an updated reconstruction image using the corrected projection data.

18. The imaging system of claim 17, wherein the at least one processor is configured to
perform forward projection on the re-mapped image volume to provide a material-based projection;
provide the error projection by applying a correction to the material-based projection to update the material-based projection to provide an updated material-based projection; and
filter by filtering at least one of:
the re-mapped image volume provided by performing the material characterization of the image volume, wherein the filtering the re-mapped image volume is performed before performing the forward projection; or
the material-based projection provided by performing the forward projection on the re-mapped image volume, wherein the filtering the material-based projection is performed before applying the correction.

19. The imaging system of claim 17, wherein the at least one processor is further configured to determine a stage at which to perform filtering based on a type of artifact to be addressed.

20. The imaging system of claim 17, wherein the at least one processor is configured to filter the forward projection data using a 1D filter.

* * * * *